United States Patent
Kojima

(10) Patent No.: US 10,842,365 B2
(45) Date of Patent: Nov. 24, 2020

(54) IMAGE PICKUP APPARATUS AND ENDOSCOPE

(71) Applicant: OLYMPUS CORPORATION, Tokyo (JP)

(72) Inventor: Kazuaki Kojima, Suwa (JP)

(73) Assignee: OLYMPUS CORPORATION, Tokyo (JP)

( * ) Notice: Subject to any disclaimer, the term of this patent is extended or adjusted under 35 U.S.C. 154(b) by 205 days.

(21) Appl. No.: 16/055,213

(22) Filed: Aug. 6, 2018

(65) Prior Publication Data

US 2018/0338674 A1    Nov. 29, 2018

Related U.S. Application Data

(63) Continuation of application No. PCT/JP2016/054698, filed on Feb. 18, 2016.

(51) Int. Cl.
*H04N 5/225* (2006.01)
*A61B 1/05* (2006.01)
*A61B 1/00* (2006.01)

(52) U.S. Cl.
CPC ............ *A61B 1/05* (2013.01); *A61B 1/00096* (2013.01); *A61B 1/051* (2013.01); *H04N 5/2254* (2013.01); *A61B 1/00009* (2013.01); *A61B 1/00018* (2013.01); *H04N 2005/2255* (2013.01)

(58) Field of Classification Search
None
See application file for complete search history.

(56) References Cited

U.S. PATENT DOCUMENTS

| | | | |
|---|---|---|---|
| 5,454,366 A | * | 10/1995 | Ito .................... A61B 1/0011 600/109 |
| 6,313,456 B1 | | 11/2001 | Miyashita et al. |
| 9,325,881 B2 | * | 4/2016 | Zen ...................... H04N 5/2251 |
| 9,402,303 B2 | * | 7/2016 | Qian .................... H05K 1/0221 |

(Continued)

FOREIGN PATENT DOCUMENTS

| | | |
|---|---|---|
| JP | H05-211997 A | 8/1993 |
| JP | H06-178757 A | 6/1994 |

(Continued)

OTHER PUBLICATIONS

International Search Report dated May 10, 2016 issued in PCT/JP2016/054698.

*Primary Examiner* — Tyler W. Sullivan
(74) *Attorney, Agent, or Firm* — Scully, Scott, Murphy & Presser, P.C.

(57) ABSTRACT

An image pickup apparatus includes: a wiring board that has a first main surface and a second main surface; an electronic components that include an image pickup device mounted on the wiring board; and conductive wires bonded to the wiring board. The wiring board includes a first area disposed in an XY plane, a second area extended from a distal end portion of the first area and disposed in an XZ plane, a third area extended from a first side surface of the first area and disposed in a YZ plane, and a fourth area extended from a distal end portion of the third area and disposed in the XZ plane. The first main surface of the second area is a distal end surface, and the image pickup device is mounted on the distal end surface.

9 Claims, 7 Drawing Sheets

(56) References Cited

U.S. PATENT DOCUMENTS

| | | | | |
|---|---|---|---|---|
| 2002/0080233 | A1* | 6/2002 | Irion | H04N 5/2253 |
| | | | | 348/65 |
| 2007/0077805 | A1* | 4/2007 | Nomura | H05K 1/028 |
| | | | | 439/331 |
| 2012/0104230 | A1* | 5/2012 | Eismann | H04N 5/2253 |
| | | | | 250/208.1 |
| 2014/0333975 | A1* | 11/2014 | Shimoda | H04N 1/02835 |
| | | | | 358/482 |
| 2014/0364694 | A1* | 12/2014 | Avron | A61B 1/00137 |
| | | | | 600/164 |
| 2015/0378144 | A1* | 12/2015 | Handte | G02B 23/2484 |
| | | | | 250/208.1 |
| 2016/0029879 | A1* | 2/2016 | Ishikawa | G02B 23/24 |
| | | | | 600/110 |
| 2017/0251913 | A1* | 9/2017 | Birnkrant | H05K 1/189 |
| 2017/0265721 | A1* | 9/2017 | Ichimura | A61B 1/04 |
| 2019/0261839 | A1* | 8/2019 | Sakai | G02B 6/423 |

FOREIGN PATENT DOCUMENTS

| | | |
|---|---|---|
| JP | H10-014868 A | 1/1998 |
| JP | H10-151112 A | 6/1998 |
| JP | 2000-210252 A | 8/2000 |
| JP | 2014-075764 A | 4/2014 |

* cited by examiner

FIG. 7
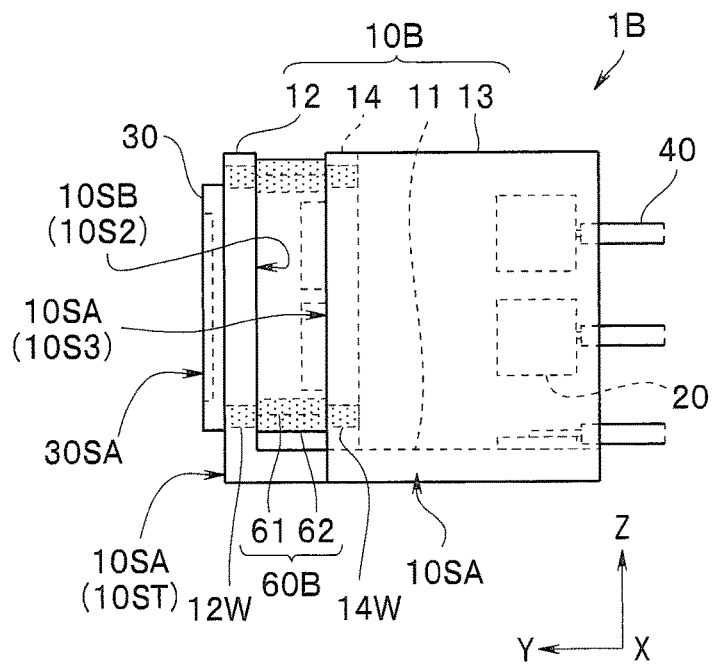
FIG. 8A
FIG. 8B
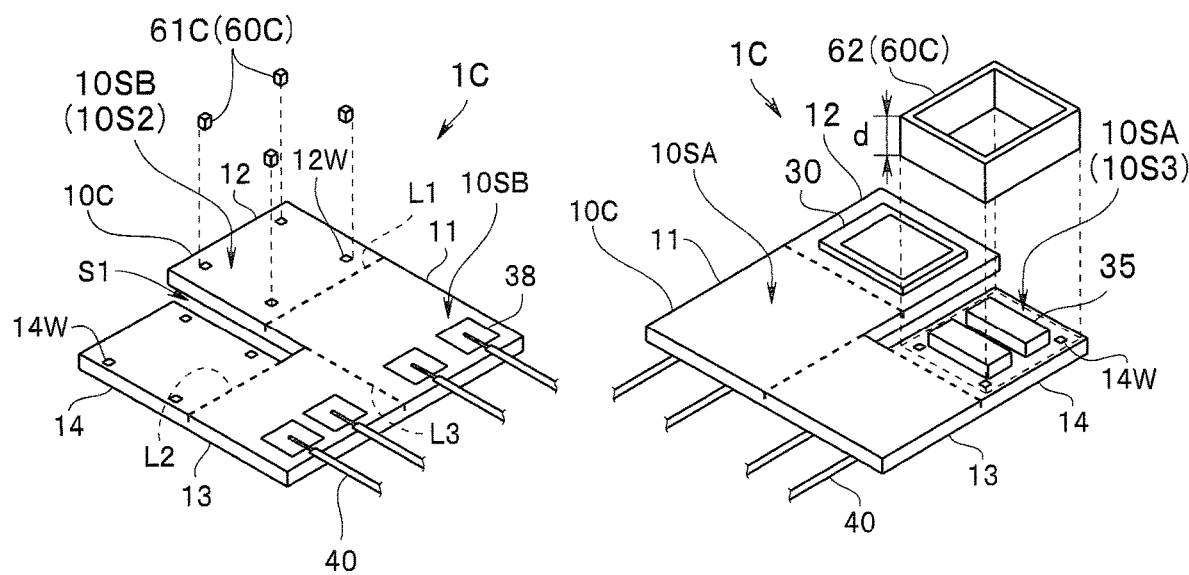

IMAGE PICKUP APPARATUS AND ENDOSCOPE

CROSS REFERENCE TO RELATED APPLICATION

This application is a continuation application of PCT/JP2016/054698 filed on Feb. 18, 2016, the entire contents of which are incorporated herein by this reference.

BACKGROUND OF INVENTION

1. Field of the Invention

The present invention relates to an image pickup apparatus including a wiring board, a plurality of electronic components that include an image pickup device mounted on the wiring board, and a plurality of conductive wires bonded to the wiring board, and relates to an endoscope including the image pickup apparatus.

2. Description of the Related Art

In an electronic endoscope having an image pickup apparatus in a rigid distal end portion, reduction in diameter and length of the image pickup apparatus is important for minimally invasive operation. The image pickup apparatus includes a wiring board mounted with a plurality of electronic components including an image pickup device.

Bending one long wiring board enables reduction in diameter of the image pickup apparatus. For example, Japanese Patent Application Laid-Open Publication No. 2014-75764 discloses an image pickup apparatus with a wiring board bent at a plurality of bent portions.

In the above image pickup apparatus, the wiring board is a cylindrical three-dimensional wiring board which is bent at several portions and formed in a rectangular shape in cross section and has an inner surface where electronic components are mounted and conductive wires are bonded. A bonding pad protruding from a side surface of the image pickup device is electrically connected to the wiring board via connection means made up of a film formed with a wiring pattern.

For further reducing the diameter of the image pickup apparatus, it is preferable to use an image pickup device of a chip-size package (CSP) type having an external electrode on a rear surface of a light receiving surface. A plurality of wiring boards are produced by dividing one large substrate into individual pieces, and for efficiently producing as many wiring boards as possible, a shape of the wiring board is also important. It is also important to facilitate a process of mounting the electronic components on the wiring board and a process of bonding the conductive wires to the wiring board.

SUMMARY OF THE INVENTION

An image pickup apparatus in an embodiment of the present invention is an image pickup apparatus including: a wiring board that has a first main surface and a second main surface opposed to the first main surface; a plurality of electronic components that include an image pickup device mounted on the wiring board; and a plurality of conductive wires bonded to the wiring board. In an XYZ orthogonal coordinate system in which a direction of an optical axis of the image pickup device is taken as a Y axis, the wiring board includes a first area disposed in an XY plane, a second area extended from a distal end portion of the first area and disposed in an XZ plane, a third area extended from a first side surface of the first area and disposed in a YZ plane, and a fourth area extended from a distal end portion of the third area and disposed in the XZ plane parallelly to the second area. The first main surface of an area, which is on a front side in the direction of the optical axis out of the second area and the fourth area, is a distal end surface, and the image pickup device is mounted on the distal end surface.

An endoscope in another embodiment of the present invention has an image pickup apparatus in a rigid distal end portion of an insertion portion, the image pickup apparatus including a wiring board that has a first main surface and a second main surface opposed to the first main surface, a plurality of electronic components that include an image pickup device mounted on the wiring board, and a plurality of conductive wires bonded to the wiring board. In an XYZ orthogonal coordinate system in which a direction of an optical axis of the image pickup device is taken as a Y axis, the wiring board includes a first area disposed in an XY plane, a second area extended from a distal end portion of the first area and disposed in an XZ plane, a third area extended from a first side surface of the first area and disposed in a YZ plane, and a fourth area extended from a distal end portion of the third area and disposed in the XZ plane parallelly to the second area. The first main surface of an area, which is on a front side in the direction of the optical axis out of the second area and the fourth area, is a distal end surface, and the image pickup device is mounted on the distal end surface.

BRIEF DESCRIPTION OF THE DRAWINGS

FIG. 7 is a side view of an image pickup apparatus in a first modification of the second embodiment.

FIG. 8A is a plan view of a wiring board of an image pickup apparatus in a second modification of the second embodiment.

FIG. 8B is a rear view of the wiring board of the image pickup apparatus in the second modification of the second embodiment.

DETAILED DESCRIPTION OF THE PREFERRED EMBODIMENTS

First Embodiment

An image pickup apparatus 1 in a first embodiment of the present invention will be described with reference to the drawings. In the following description, the drawings are schematic, and a relationship between a thickness and a width of each member, a ratio of thicknesses of respective members, the number of electrode pads, arrangement pits, and the like are different from real ones. Each drawing includes a part which is different in dimensional relation or ratio among the drawings. Further, some components are omitted in illustration.

Note that the following drawings are shown using an XYZ orthogonal coordinate system in which a direction of an optical axis O of an image pickup device is taken as the Y axis. "A front side in the direction of the optical axis" means a direction of an object, namely a direction in which a value of the Y coordinate increases. A direction in which an image pickup device is disposed, namely, a direction in which a value of the Y axis increases is referred to as a "front (distal end)" direction.

Figure 1:
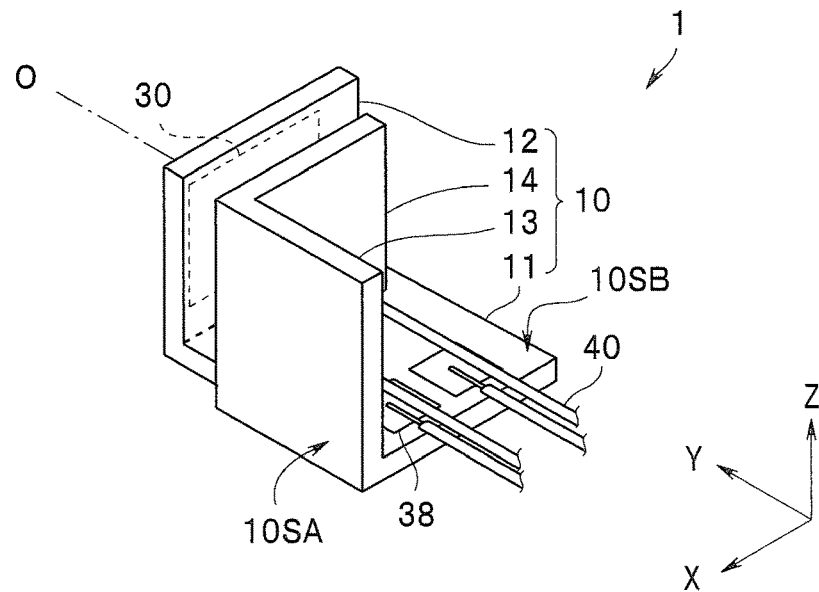
FIG. 1 is a perspective view of an image pickup apparatus in a first embodiment.
Figure 2:
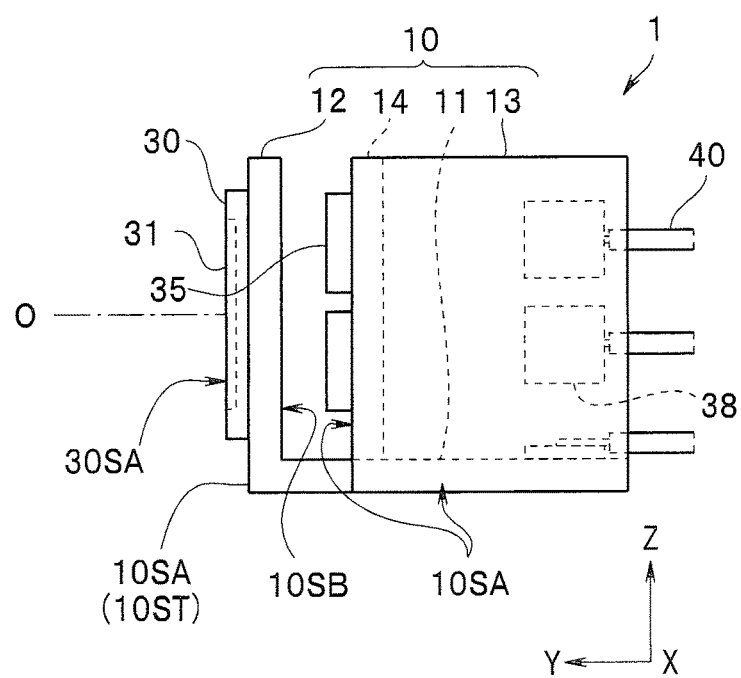
FIG. 2 is a side view of the image pickup apparatus in the first embodiment.

As shown in FIGS. 1 and 2, an image pickup apparatus 1 includes a wiring board 10, a plurality of electronic components 35 including an image pickup device 30, and a plurality of conductive wires 40.

The image pickup device 30 is made up of a semiconductor such as silicon, and light received from a light receiving surface 30SA is received by a light receiving portion 31, such as a CCD or CMOS light reception circuit, and converted into an electric signal. On a rear surface of the CSP-type image pickup device 30, which is opposed to the light receiving surface 30SA, a plurality of external electrodes (not shown), electrically connected to the light receiving portion 31 via such as through wires (not shown), are disposed. A drive signal inputted into the light receiving portion 31 and an image pickup signal outputted by the light receiving portion 31 are transmitted via the respective external electrodes.

As a protective member of the light receiving portion 31, a cover glass may be disposed, and further, a light receiving optical system may be disposed.

The wiring board 10 has a first main surface 10SA and a second main surface 10SB which is opposed to the first main surface 10SA. All the plurality of electronic components 35 including the image pickup device 30 are mounted on the first main surface 10SA of the wiring board 10. All the plurality of conductive wires 40 are bonded to the second main surface 10SB of the wiring board 10.

The wiring board 10 is a flexible wiring board with polyimide taken as a base, for example. The wiring board 10 is originally one tabular plate, and then bent at a plurality of bent portions L1, L2, L3 (see FIGS. 3A and 3B) to become a three-dimensional wiring board, as described later.

That is, the wiring board 10 includes a first area 11 disposed in an XY plane, a second area 12 disposed in an XZ plane, a third area 13 disposed in a YZ plane, and a fourth area 14 disposed in the XZ plane parallelly to the second area 12. The second area 12 is extended from a distal end portion of the first area. The third area 13 is extended from a first side surface of the first area 11. The fourth area 14 is extended from a distal end portion of the third area 13.

The first main surface 10SA of the second area 12 is a distal end surface 10ST, and the external electrodes (not shown) on the rear surface of the image pickup device 30 are bonded to electrodes 36 on the distal end surface 10ST.

The conductive wires 40 are bonded to electrodes 38 in the first area 11 and the third area 13 of the wiring board 10.

Next, a manufacturing method for the image pickup apparatus 1 will be described using FIGS. 3A, 3B and 4. As already described, the wiring board 10 is originally one tabular flexible wiring board in a substantially rectangular shape, having the first main surface 10SA and the second main surface 10SB.

In the wiring board 10, the first area 11 and the second area 12 are divided by the bent portion L1. The third area 13 and the fourth area 14 are divided by the bent portion L2. The first area 11 and the third area 13 are divided by the bent portion L3. The second area 12 and the fourth area 14 are divided by a slit S1.

In the wiring board 10, the substrate may be a non-flexible substrate made of glass epoxy resin, or the like, but at least the bent portions L1, L2, L3 need to be flexible.

Figure 3A:
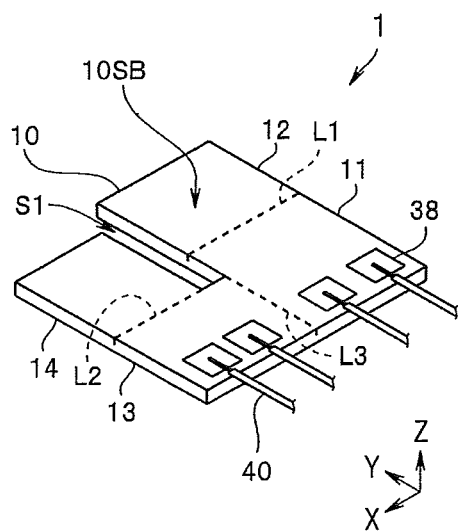
FIG. 3A is a plan view of a wiring board of the image pickup apparatus in the first embodiment.
Figure 3B:
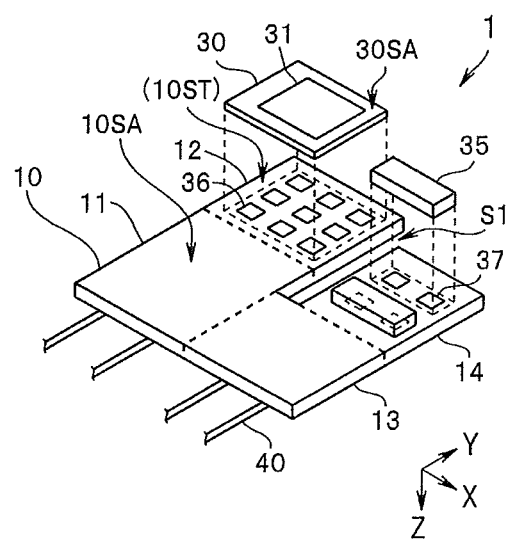
FIG. 3B is a rear view of the wiring board of the image pickup apparatus in the first embodiment.

As shown in FIG. 3B, the electrodes 36 are disposed in the second area 12, and electrodes 37 are disposed in the fourth area 14 of the first main surface 10SA. In the meantime, as shown in FIG. 3A, the electrodes 38 are disposed in the first area 11 and the third area 13 of the second main surface 10SB. The image pickup device 30 is mounted on the electrodes 36, and the conductive wires 40 are bonded to the electrodes 38.

That is, the wiring board 10 is a double-sided wiring board having electrodes on the first main surface 10SA and the second main surface 10SB, but the plurality of electronic components including the image pickup device 30 are mounted on the first main surface 10SA and the conductive wires 40 are bonded to the second main surface 10SB where the electronic components are not mounted.

Figure 4:
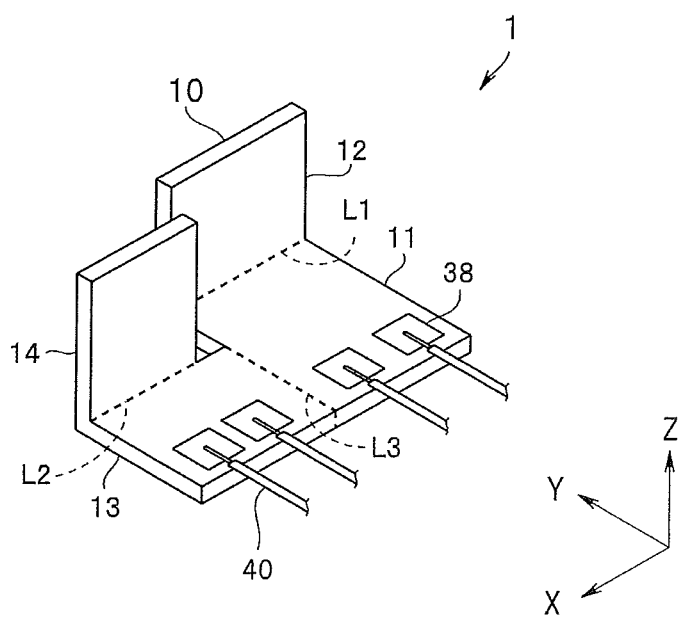
FIG. 4 is a perspective view of the wiring board of an image pickup apparatus in the first embodiment.

Next, as shown in FIG. 4, the second area 12 and the fourth area 14 of the wiring board 10, where the electronic components are mounted and the conductive wires 40 are bonded, are bent at right angles to the XY plane, where the first area 11 and the third area 13 are located, via the bent portions L1, L2. Further, the third area 13 is bent at right angles to the XY plane, where the first area 11 is located, via the bent portion L3 to form the three-dimensional wiring board shown in FIGS. 1 and 2.

Note that the bent portions L1, L2, L3 may be curved. When the wiring board 10 is a flexible wiring board, each area of the wiring board may not be perfect tabular, but may be curved. In other words, an entire surface of each area of the wiring board may not be located on each plane. That is, the wiring board 10 may have a cylindrical shape, with a cross section not being rectangular but being substantially circular.

As shown in FIGS. 3A and 3B, in the image pickup apparatus 1, the wiring board 10 is substantially rectangular at first. Hence a larger number of wiring boards can be efficiently produced from one large substrate. On the wiring board 10, the electronic components are mounted only on one surface, and hence the mounting is easily performed. Further, the conductive wires 40 are bonded only to one surface, and hence the bonding is easily performed. Moreover, with the wiring board 10 being the three-dimensional wiring board, the electronic components are disposed and the conductive wires 40 are bonded efficiently in a narrow space, so the image pickup apparatus 1 has a small diameter and a small length.

Although the first main surface 10SA of the second area 12 is the distal end surface LOST in the image pickup apparatus 1, needless to say, the first main surface 10SA of the fourth area 14 may be the distal end surface 10ST depending on design of the wiring board. That is, the first main surface 10SA of an area, which is on a front side in the direction of the optical axis, which is either the second area 12 or the fourth area 14, is the distal end surface 10ST.

Second Embodiment

Next, an image pickup apparatus 1A of a second embodiment will be described. Because the image pickup apparatus 1A is similar to and has the same effect as the image pickup apparatus 1, the same components are provided with the same reference numerals as in the image pickup apparatus 1, and description of such components is omitted.

Figure 5:
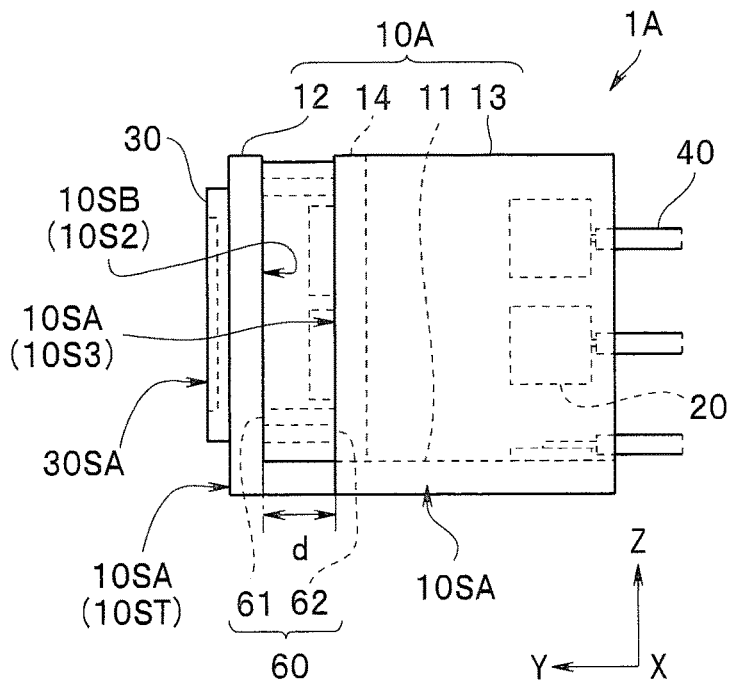
FIG. 5 is a side view of an image pickup apparatus in a second embodiment.
Figure 6A:
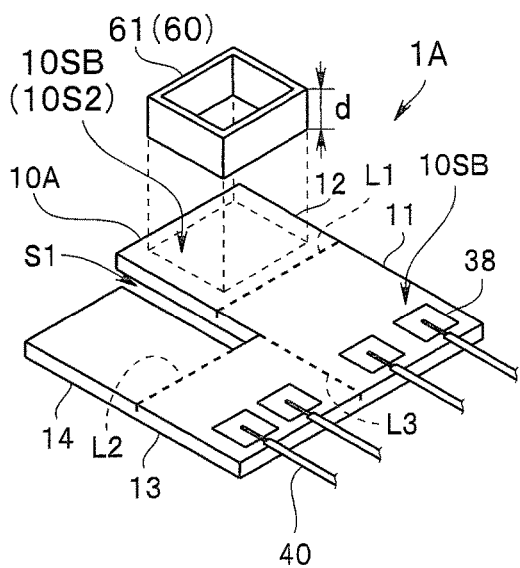
FIG. 6A is a plan view of a wiring board of the image pickup apparatus in the second embodiment.
Figure 6B:
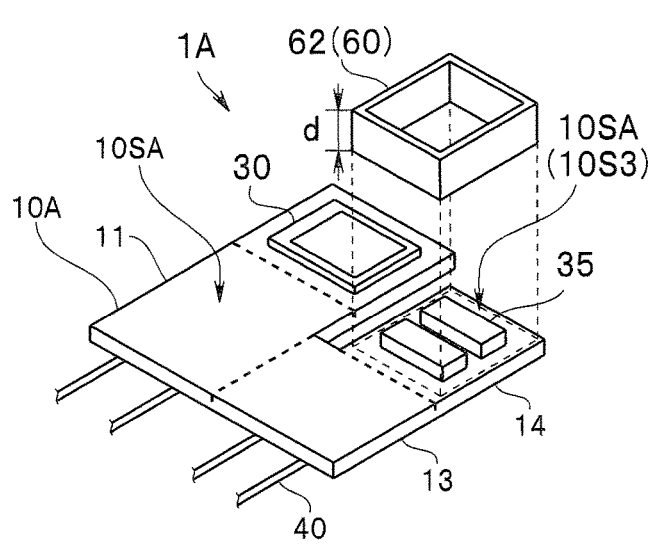
FIG. 6B is a rear view of the wiring board of the image pickup apparatus in the second embodiment.

As shown in FIGS. 5, 6A, and 6B, the image pickup apparatus 1A has a spacer 60 made up of a first convex portion 61 and a second convex portion 62 each having a frame shape. A space d between the second area 12 and the fourth area 14 is defined by the spacer 60.

As shown in FIG. 6A, the first convex portion 61 is disposed in the second area 12 on the second main surface 10SB of the wiring board 10A. In the meantime, as shown in FIG. 6B, the second convex portion 62 is disposed in the fourth area 14 of the first main surface 10SA. A height of each of the first convex portion 61 and the second convex portion 62 is d. Hence the first convex portion 61 and the second convex portion 62 abut on the second main surface 10SB of the second area 12 and the second main surface 10SB of the fourth area 14.

Further, the first convex portion 61 is designed such that an outer wall of the first convex portion 61 abuts on an inner wall of the second convex portion 62. Therefore, by fitting the first convex portion 61 with the second convex portion 62, a positional relationship between the second area 12 and the fourth area 14 is defined automatically.

The wiring board 10A is easily assembled because the space d and the positional relationship are defined by the first convex portion 61 and the second convex portion 62 which are the spacer 60.

Note that it goes without saying that when the height of either the first convex portion 61 or the second convex portion 62 is the height d, the height of the other may be lower than the height d. That is, when either convex portion abuts on the opposing surface, the space d is defined. The space can be defined by only one convex portion. However, combining two convex portions to constitute the spacer 60 is preferable because of easiness to position two surfaces.

Here, the first convex portion 61 and the second convex portion 62 in the frame shape are made of a conductive material such as copper. Hence, electromagnetic waves, generated by the electronic components 35 mounted inside the second convex portion 62 of the fourth area 14 and located inside the fitted first convex portion 61, are shielded by the first convex portion 61 and the second convex portion 62 and thus hardly emitted to the outside.

Needless to say, an image pickup apparatus, in which at least either the first convex portion 61 or the second convex portion 62 has the frame shape and is made of a conductive material abutting on the opposing surface and the opposed surface, has the same effect as the effect of the image pickup apparatus 1A.

Here, the second main surface 10SB of the second area 12 is the opposing surface which is a rear surface of the distal end surface 10ST. The first main surface 10SA of the fourth area 14 is the opposed surface disposed parallelly to the opposing surface. In other words, the spacer 60 abuts on the opposing surface which is the rear surface of the distal end surface 10ST and on the opposed surface disposed parallelly to the opposing surface.

When the first main surface 10SA of the fourth area 14 is the distal end surface 10ST, the second main surface 10SB of the fourth area 14 is the opposing surface which is the rear surface of the distal end surface 10ST. The first main surface 10SA of the second area 12 is disposed parallelly to the opposing surface.

That is, in the image pickup apparatus of the present embodiment, the space between the opposing surface and the opposed surface is defined by the spacer made up of the first convex portion 61 disposed on the opposing surface, which is the rear surface of the distal end surface, and the second convex portion 62 disposed on the opposed surface disposed parallelly to the opposing surface and abutting on the first convex portion 61.

Modifications of Second Embodiment

Next, image pickup apparatuses 1B, 1C of first and second modifications of the second embodiment will be described. Because the image pickup apparatuses 1B, 1C are similar to and have the same effect as the image pickup apparatus 1A, the same components are provided with the same reference numerals as in the image pickup apparatus 1A, and description of such components is omitted.

First Modification of Second Embodiment

As shown in FIG. 7, a wiring board 10B of the image pickup apparatus 1B includes: a first through wire 12W penetrating between the distal end surface 10ST (the first main surface 10SA of the second area 12) and the opposing surface (the second main surface 10SB of the second area 12); and a second through wire 14W penetrating between the opposed surface (the first main surface 10SA of the fourth area 14) and the rear surface of the opposed surface (the second main surface 10SB of the fourth area 14).

As in the image pickup apparatus 1A, each of the first convex portion 61 and the second convex portion 62 in the frame shape is made of a conductive material. The first convex portion 61 is bonded with the first through wire 12W, and the second convex portion 62 is bonded to the second through wire 14W. That is, the spacer 60B made of the conductive material is bonded with the first through wire 12W and the second through wire 14W.

Therefore, as shown in FIG. 7, heat generated by the image pickup device 30 is transmitted rearward via the first through wire 12W, the spacer 60B, and the second through wire 14W, any of which is made of the conductive material being a high-heat conductor. The image pickup apparatus 1B is thus free from risk of deterioration in the image pickup device 30 due to a temperature rise and of degradation in image quality due to thermal noise.

Second Modification of Second Embodiment

As shown in FIGS. 8A and 8B, a spacer 60C of the image pickup apparatus 1C is made up of four columnar first convex portions 61C disposed on the second main surface 10SB of the wiring board 10C and the second convex portion 62 in the frame shape disposed on the first main surface 10SA. The first convex portion 61C is disposed so as to be fitted with corner portions of inner walls of the second convex portions 62.

The space d between the second area 12 and the fourth area 14 is defined by a height of the second convex portion 62. The positioning is performed by fitting the first convex portion 61C with the second convex portion 62.

That is, as long as the spacer made up of two convex portions fitted with each other is used, the positioning as well as definition of the space can be performed.

Further, when the second convex portion 62 is made of the conductive material in the frame shape, the spacer has a shield effect. Needless to say, the first through wire 12W, the second convex portion 62, and the second through wire 14W become heat transmission channels.

Third Embodiment

Next, an image pickup apparatus 1D of a third embodiment will be described. Because the image pickup apparatus 1D is similar to and has the same effect as the image pickup apparatus 1, the same components are provided with the same reference numerals as in the image pickup apparatus 1, and description of such components is omitted.

Figure 9:
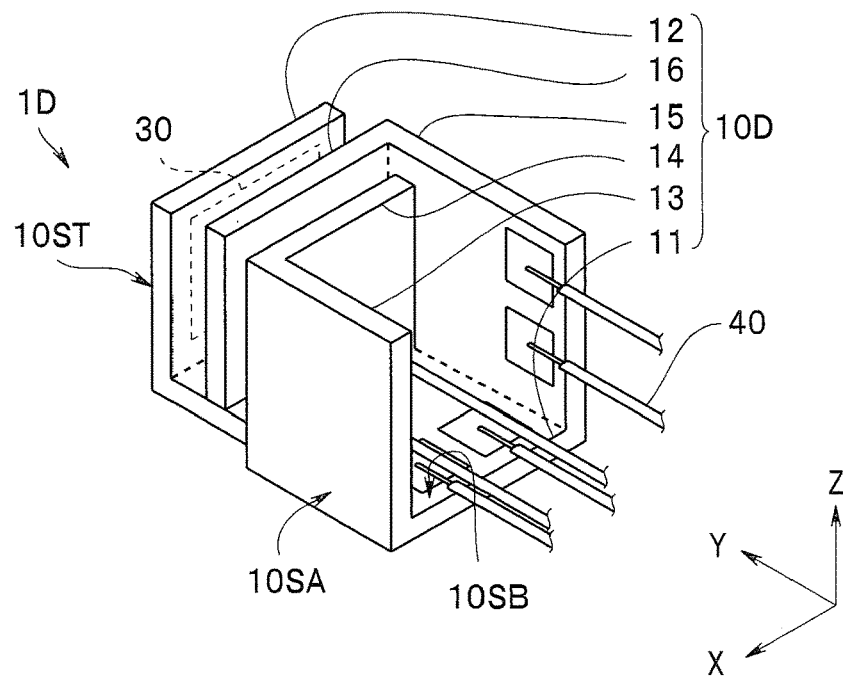
FIG. 9 is a perspective view of an image pickup apparatus in a third embodiment.
Figure 10A:
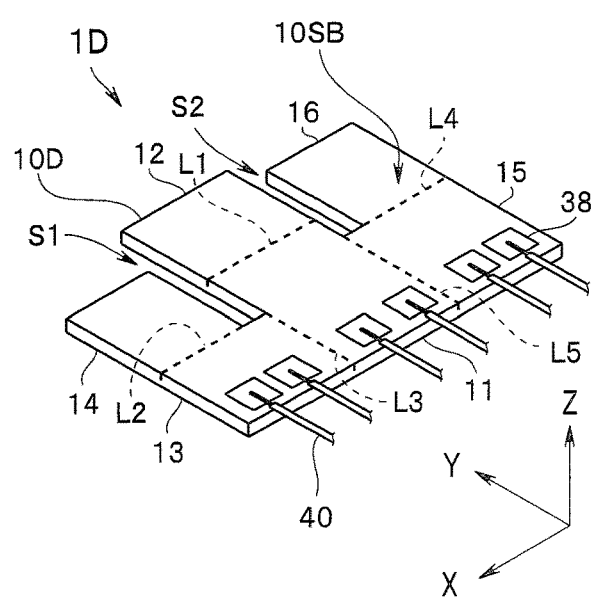
FIG. 10A is a rear view of a wiring board of the image pickup apparatus in the third embodiment.

As shown in FIGS. 9 and 10A, a wiring board 10D of the image pickup apparatus 1D further includes, in addition to the components of the wiring board 10, a fifth area 15 extended from a second side surface which is opposed to the first side surface of the first area 11, and a sixth area 16 extended from a distal end portion of the fifth area 15.

The fifth area 15 is disposed on the YZ plane parallelly to the third area 13. The sixth area 16 is disposed on the XZ plane parallelly to the second area 12 and the fourth area 14.

The first area 11 and the fifth area 15 are divided by a bent portion L5, and the fifth area 15 and the sixth area 16 are divided by a bent portion L4.

Figure 10B:
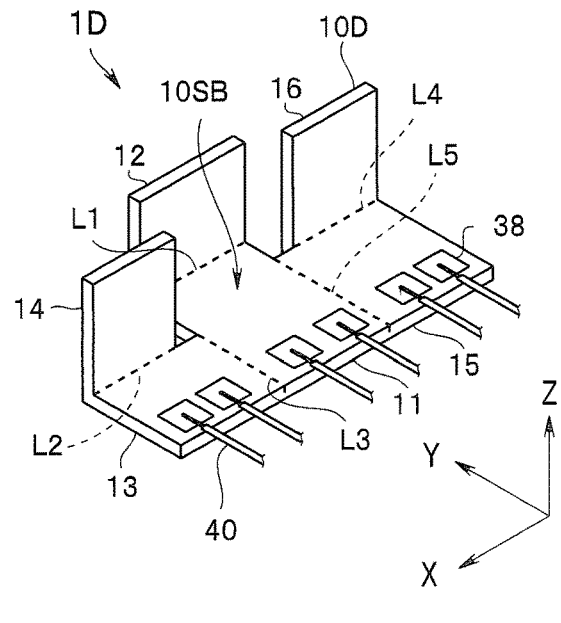
FIG. 10B is a rear view of the wiring board of the image pickup apparatus in the third embodiment.

As shown in FIG. 10B, the second area 12, the fourth area 14, and the sixth area 16 of the wiring board 10, where the electronic components are mounted and the conductive wires 40 are bonded, are bent at right angles to the XY plane, where the first area 11 is located, via the bent portions L1, L2, L4. Further, the third area 13 is bent at right angles to the XY plane where the first area 11 is located via the bent portion L3, and the fifth area 15 is bent at right angles to the XY plane where the first area 11 is located via the bent portion L5, so that the wiring board 10D becomes a three-dimensional structure shown in FIG. 9.

The image pickup apparatus 1D has an outer diameter almost the same as an outer diameter of the image pickup apparatus 1, but the electrode 38 bonded with the conductive wire 40 can also be disposed in the fifth area 15. Therefore, for example, a conductive wire for power transmission and a conductive wire for signal transmission are not disposed close to each other, which makes operation more stable.

Needless to say, the image pickup apparatus 1D has a similar effect to the effect of the image pickup apparatuses 1A to 1C by including the spacer.

Fourth Embodiment

Next, an image pickup apparatus 1E of a fourth embodiment will be described. Because the image pickup apparatus 1E is similar to and has the same effect as the image pickup apparatus 1D, the same components are provided with the same reference numerals as in the image pickup apparatus 1D, and description of such components is omitted.

Figure 11:
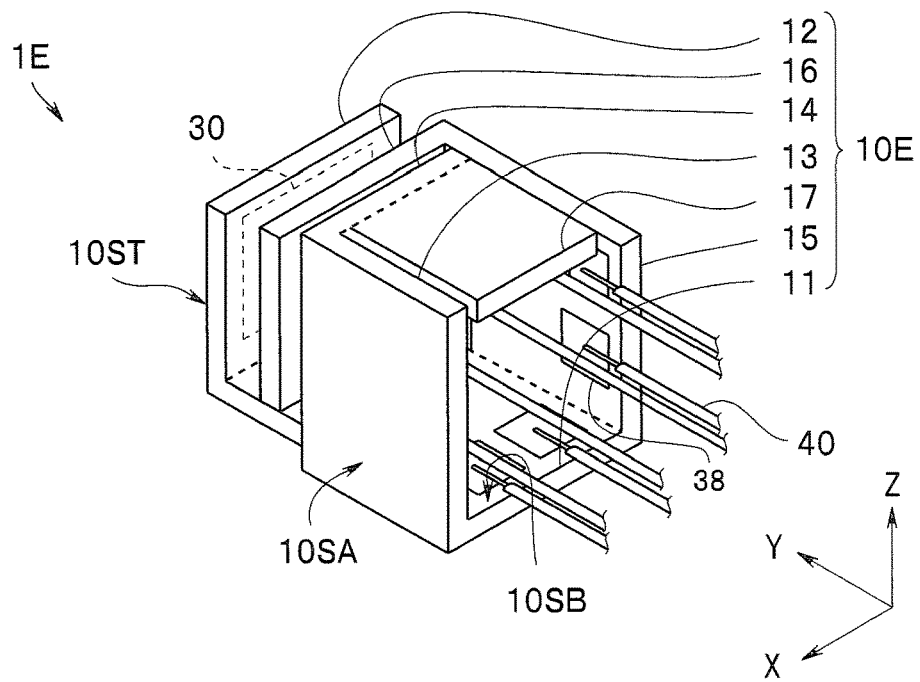
FIG. 11 is a perspective view of an image pickup apparatus in a fourth embodiment.
Figure 12A:
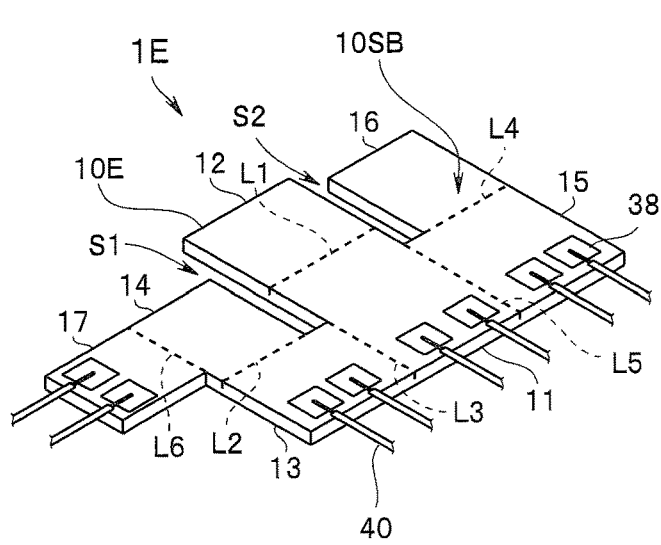
FIG. 12A is a rear view of a wiring board of the image pickup apparatus in the fourth embodiment.
Figure 12B:
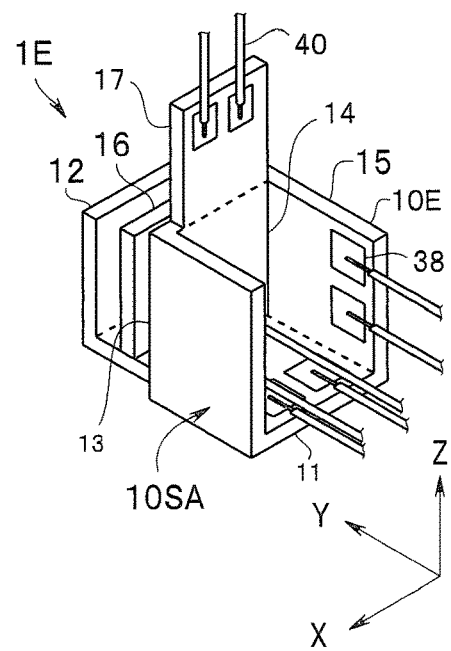
FIG. 12B is a rear view of a wiring board of the image pickup apparatus in the fourth embodiment.

As shown in FIGS. 11, 12A, and 12B, a wiring board 10E of the image pickup apparatus 1E further includes, in addition to the components of the wiring board 10D, a seventh area 17 extended from a side surface of the fourth area 14. The fourth area 14 and the seventh area 17 are divided by a bent portion L6.

For example, by bending the seventh area 17 of the wiring board 10E, bent as in the wiring board 10D, at right angles via a bent portion L6, the seventh area 17 is disposed on the XY plane parallelly to the first area 11.

The image pickup apparatus 1E has an outer diameter almost the same as outer diameters of the image pickup apparatuses 1, 1D, but the electrode 38 bonded with the conductive wire 40 can also be disposed in the seventh area 17. This makes operation more stable.

It goes without saying that the image pickup apparatus 1E has a similar effect to the effect of the image pickup apparatuses 1A to 1C by including the spacer.

Fifth Embodiment

Figure 13:
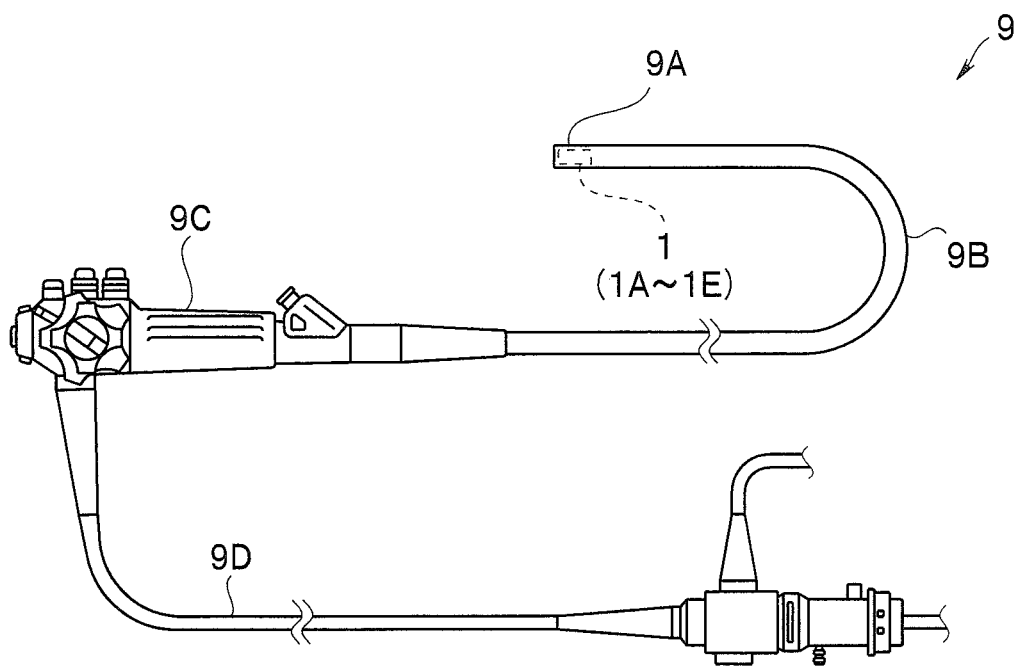
FIG. 13 is a perspective view of an endoscope in a fifth embodiment.

As shown in FIG. 13, an endoscope 9 of the fifth embodiment has any of the already described image pickup apparatuses 1, 1A to 1E in a rigid distal end portion 9A of an insertion portion 9B.

The endoscope 9 includes an elongated insertion portion 9B inserted through the inside of a living body, an operation portion 9C, and a universal cable 9D, through which an electric cable and the like are inserted. Note that the endoscope 9 of the embodiment is a so-called flexible endoscope, but even a so-called rigid endoscope with the insertion portion 9B being rigid also has an effect described below.

The endoscope 9 has any of the image pickup apparatuses 1, 1A to 1E, each having a small diameter and a small length and easy to manufacture, in the rigid distal end portion 9A, and hence the endoscope 9 is minimally invasive and easy to manufacture.

The present invention is not limited to the embodiments, the modifications, or the like described above, and various modifications, alterations, combinations, and the like are possible in a scope where no change is made on the gist of the present invention.

What is claimed is:

1. An image pickup apparatus comprising:
    a wiring board having a first main surface and a second main surface opposed to the first main surface;
    a plurality of electronic components including an image pickup sensor mounted on the wiring board; and
    a plurality of electrodes disposed on one or more of the first main surface and second main surface, the plurality of electrodes being each being configured to bond with a conductive wire,
    wherein
    in an XYZ orthogonal coordinate system in which a direction of an optical axis of the image pickup device is taken as a Y axis, the wiring board includes a first portion disposed in an XY plane, a second portion extended from a distal end portion of the first portion about a first bend line, the second portion being disposed in an XZ plane, a third portion extended from a first side surface of the first portion about a second bend line orthogonal to the first bend line, the third portion being disposed in a YZ plane, and a fourth portion extended from a distal end portion of the third portion about a third bend line orthogonal to each of the first and second bend lines, the fourth portion being disposed in the XZ plane parallel to the second portion, each of the second portion and fourth portion having distal and proximal surfaces opposing each other, and the image pickup sensor is mounted on a distal-most one of the distal surface of the second portion and the distal surface of the fourth portion;

the second portion is folded from the distal end portion of the first portion about the first bend line;

the third portion is folded from the first side surface of the first portion about the second bend line; and the fourth portion is folded from the distal end portion of the third portion about the third bend line.

2. The image pickup apparatus according to claim 1, wherein the plurality of electronic components are mounted on the first main surface, and the plurality of electrodes are disposed on the second main surface on which none of the plurality of electronic components are mounted.

3. The image pickup apparatus according to claim 1, comprising a spacer disposed between the proximal surface of the one of the second portion and the fourth portion having the image pickup sensor and the distal surface of the other of the second and fourth portions.

4. The image pickup apparatus according to claim 3, wherein the spacer has a frame shape and the spacer comprises a conductive material.

5. The image pickup apparatus according to claim 3, further comprising:

a first through wire penetrating between the distal surface and the proximal surface of the one of the second portion and the fourth portion having the image pickup sensor, and a second through wire penetrating between the distal surface and the proximal surface of the other of the second and fourth portions, wherein the spacer comprises a conductive material, the spacer having a first end bonded to the first through wire and a second end bonded to the second through wire.

6. The image pickup apparatus according to claim 3, wherein the spacer having a first convex portion disposed on the proximal surface of the one of the second portion and the fourth portion having the image pickup sensor and a second convex portion disposed on the distal surface of the other of the second and fourth portions such that one of the first and the second convex portions fits within the other of the first and second convex portions.

7. The image pickup apparatus according to claim 1, wherein the wiring board further comprises:

a fifth portion extended from a second side surface which is opposed to the first side surface of the first portion and disposed on the YZ plane parallel to the third portion, and a sixth portion extended from a distal end portion of the fifth and disposed on the XZ plane parallel to the second portion and to the fourth portion.

8. The image pickup apparatus according to claim 1, wherein the wiring board further comprises a seventh portion extended from a side surface of the fourth portion, and the seventh portion is disposed on one of the XY plane parallel to the first portion and the XZ plane parallel to the fourth portion.

9. An endoscope comprising:

a rigid distal end portion; and the image pickup apparatus according to claim 1 disposed in the rigid distal end portion.

* * * * *